(12) United States Patent
Unnerstall

(10) Patent No.: US 11,127,014 B2
(45) Date of Patent: Sep. 21, 2021

(54) SYSTEMS AND METHODS FOR ANALYZING SLEEP DATA AND SLEEP PATTERN DATA

(71) Applicant: MASTERCARD INTERNATIONAL INCORPORATED, Purchase, NY (US)

(72) Inventor: Rick Unnerstall, O'Fallon, MO (US)

(73) Assignee: MASTERCARD INTERNATIONAL INCORPORATED, Purchase, NY (US)

( * ) Notice: Subject to any disclaimer, the term of this patent is extended or adjusted under 35 U.S.C. 154(b) by 509 days.

(21) Appl. No.: 15/838,129

(22) Filed: Dec. 11, 2017

(65) Prior Publication Data

US 2019/0180283 A1 Jun. 13, 2019

(51) Int. Cl.
*G06Q 20/40* (2012.01)
*A61B 5/00* (2006.01)

(52) U.S. Cl.
CPC ....... *G06Q 20/4016* (2013.01); *A61B 5/4812* (2013.01); *G06Q 20/4014* (2013.01); *A61B 2503/12* (2013.01)

(58) Field of Classification Search
CPC .................................................. G06Q 20/4016
USPC .......................................................... 705/44
See application file for complete search history.

(56) References Cited

U.S. PATENT DOCUMENTS

| 6,914,968 | B1 | 7/2005 | Ryley et al. |
| 7,620,599 | B2 | 11/2009 | Degen et al. |
| 7,958,228 | B2 | 6/2011 | Riise et al. |
| 8,478,692 | B2 | 7/2013 | Carlson et al. |
| 9,094,388 | B2 | 7/2015 | Tkachev |
| 9,357,384 | B2 | 5/2016 | Ibrahim et al. |
| 9,536,071 | B2 | 1/2017 | Turgeman |
| 10,303,869 | B1 * | 5/2019 | Duke ...................... G06F 21/36 |
| 2006/0010072 | A1 | 1/2006 | Eisen |
| 2012/0226579 | A1 | 9/2012 | Ha et al. |
| 2014/0250009 | A1 | 9/2014 | Carlson |
| 2015/0213246 | A1 * | 7/2015 | Turgeman ............... G06F 21/32 726/23 |

(Continued)

OTHER PUBLICATIONS

Web Article: "Machine learning and big data know it wasnt you who just swiped your credit card", Site: The Conversation, Nov. 25, 2015, 4 pps.: http://theconversation.com/machine-learning-and-big-data-know-it-wasnt-you-who-just-swiped-your-credit-card-48561.

(Continued)

*Primary Examiner* — Cho Kwong
(74) *Attorney, Agent, or Firm* — Armstrong Teasdale LLP

(57) ABSTRACT

A sleep pattern analyzer (SPA) system for capturing and analyzing sleep data and sleep pattern data is provided. The SPA system is configured to receive sleep data associated with a user, the sleep data including a registered user identifier and at least one sleep time stamp, and store the sleep data in a sleep pattern database. The SPA system is also configured to receive transaction data for a transaction initiated by a consumer with a merchant. The SPA system is further configured to match the consumer identifier to the registered user identifier, generate a fraud notification message when the transaction time stamp overlaps with the at least one sleep time stamp, and transmit the fraud notification message to at least one of an issuer, the merchant, and the consumer associated with the consumer identifier.

20 Claims, 6 Drawing Sheets

(56) References Cited

U.S. PATENT DOCUMENTS

2016/0019546 A1   1/2016   Eisen

OTHER PUBLICATIONS

Patrick Altoft, Web Article: "Five Ways to Detect Fraud Using Geolocation", Site: BRANDED3, dated Dec. 15, 2008, 6 pps.: https://www.branded3.com/blog/five-ways-to-detect-fraud-using-geolocation/.

* cited by examiner

SYSTEMS AND METHODS FOR ANALYZING SLEEP DATA AND SLEEP PATTERN DATA

BACKGROUND

The field of the present disclosure relates generally to capturing and analyzing sleep data and sleep pattern data, and more specifically, to network-based systems and methods for analyzing sleep data and sleep pattern data and using such data to identify fraudulent activities.

Advances in technology have spawned a plethora of sleep tracking devices and sleep tracking applications. These tracking devices and applications are configured to monitor and capture a range of data. The data may be associated with a user's bodily motion, physical activity, heart rate, breathing pattern, location, time, skin conductivity, sound, brain activity, and the like. Capturing such data enables the tracking devices and applications to determine the time and location where a user is likely asleep. However, at present, such data is not typically collected at a central location, such as a central database server, for evaluation and analysis. The evaluation and analysis of such data may assist various industries in detection of potentially fraudulent activity.

Payment accounts and payment cards (e.g., debit cards, credit cards, etc.) may be subject to fraudulent activity, such as through theft of the payment cards and data breaches. These compromised payment accounts and payment cards may be used in fraudulent transactions with merchants to purchase goods and/or services at the expense of the authorized users of the compromised payment accounts and payment cards (e.g., cardholders). If a fraudulent transaction is contested, for example, by an authorized user of a payment card (e.g., legitimate cardholder), liability of the fraudulent transaction is determined, and the liable party is responsible for reimbursing the legitimate cardholder for the fraudulent transaction. In some embodiments, the liable party may be a merchant associated with the fraudulent purchase. In other embodiments, the liable party may be the issuing institutions (e.g., issuer banks) of the payment accounts and payment cards.

In at least some known payment processing systems and in effort to prevent fraudulent purchases, parties involved in transactions use fraud scoring systems. If a transaction fits a certain pattern, it may be scored as having a high risk of fraud, and thus, the transaction may be declined by one or more parties in the transaction. For example, payment transactions originating in geographical locations outside the cardholder's typical location, e.g., certain foreign countries, have an increased probability of being fraudulent, and may be flagged for additional verification. With respect to present systems, card-present and card-not-present (CNP) transactions cannot be initiated if the legitimate cardholder is asleep. It would be desirable to have a fraud detection system that can determine when the legitimate cardholder is asleep.

BRIEF DESCRIPTION

In one aspect, sleep pattern analyzer (SPA) system for capturing and analyzing sleep data and sleep pattern data is provided. The SPA system includes at least one sleep pattern analyzer (SPA) computing device that includes a processor communicatively coupled to a memory and is configured to receive sleep data associated with a user, the sleep data including a registered user identifier and at least one sleep time stamp, and store the sleep data in a sleep pattern (SP) database. The SPA computing device is also configured to receive transaction data for a transaction initiated by a consumer with a merchant, the transaction data including a consumer identifier, and a transaction time stamp, and compare the transaction data to the stored sleep data. The SPA computing device is further configured to match the consumer identifier to the registered user identifier, generate a fraud notification message when the transaction time stamp overlaps with the at least one sleep time stamp, and transmit the fraud notification message to at least one of an issuer, the merchant, and the consumer associated with the consumer identifier.

In another aspect, a computer-implemented method for capturing and analyzing sleep data and sleep pattern data is provided. The method is performed using at least one sleep pattern analyzer (SPA) computing device that includes at least one processor in communication with at least one memory device. The method includes receiving sleep data associated with a user, the sleep data including a registered user identifier and at least one sleep time stamp, and storing the sleep data in a sleep pattern (SP) database. The method also includes receiving transaction data for a transaction initiated by a consumer with a merchant, the transaction data including a consumer identifier, and a transaction time stamp, and comparing the transaction data to the stored sleep data. The method further includes matching the consumer identifier to the registered user identifier, generating a fraud notification message when the transaction time stamp overlaps with the at least one sleep time stamp, and transmitting the fraud notification message to at least one of an issuer, the merchant, and the consumer associated with the consumer identifier.

In yet another aspect, a non-transitory computer readable medium that includes executable instructions for capturing and analyzing sleep data and sleep pattern data is provided. When the computer executable instructions are executed by at least one sleep pattern analyzer (SPA) computing device that includes at least one processor in communication with at least one memory device, the computer executable instructions cause the at least one SPA computing device to receive sleep data associated with a user, the sleep data including a registered user identifier and at least one sleep time stamp, and store the sleep data in a sleep pattern (SP) database. The computer executable instructions also cause the at least one SPA computing device to receive transaction data for a transaction initiated by a consumer with a merchant, the transaction data including a consumer identifier, and a transaction time stamp, and compare the transaction data to the stored sleep data. The computer executable instructions further cause the at least one SPA computing device to match the consumer identifier to the registered user identifier, generate a fraud notification message when the transaction time stamp overlaps with the at least one sleep time stamp, and transmit the fraud notification message to at least one of an issuer, the merchant, and the consumer associated with the consumer identifier.

BRIEF DESCRIPTION OF THE DRAWINGS

FIG. 1 is a schematic diagram illustrating an example sleep pattern analyzer (SPA) system for capturing and analyzing sleep data and sleep pattern data in communication with a multi-party payment processing system for processing payment-by-card transactions FIG. 2 is a schematic diagram illustrating the example SPA system for capturing and analyzing sleep data and sleep pattern data in accordance with one embodiment of the disclosure.

FIG. 3 illustrates an example configuration of a user computing device shown in FIG. 2, in accordance with one embodiment of the present disclosure.

FIG. 4 illustrates an example configuration of a server system shown in FIG. 2, in accordance with one embodiment of the present disclosure.

FIG. 5 is a flow chart showing a process for building fraud scores by correlating encrypted on-device biometric data with contextual transactional data and device data using the system shown in FIG. 2.

FIG. 6 is a diagram of components of one or more example computing devices that may be used in the system shown in FIG. 2.

DETAILED DESCRIPTION

Figure 1:
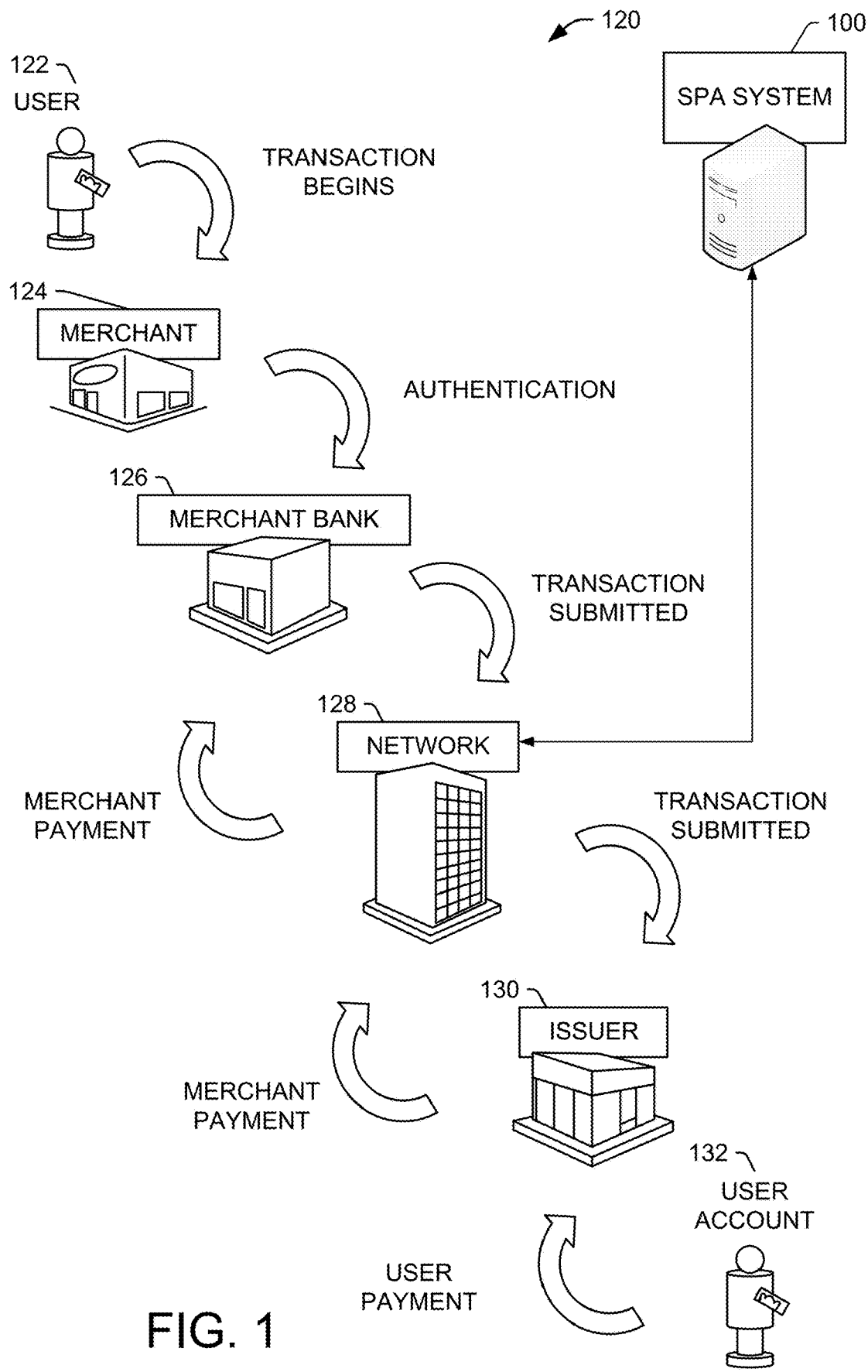
FIGS. 1-6 show example embodiments of the methods and systems described herein.

Systems and methods according to this disclosure are directed to reducing fraudulent activity associated with payment card transactions, and more specifically, to network-based systems and methods configured to reduce fraudulent payment activity using sleep pattern data associated with the legitimate user (also referred to herein as a "cardholder" or "actual cardholder" or legitimate cardholder") of the payment card. In other words, the systems and methods described herein are configured to build a sleep profile of the user (e.g., actual cardholder) using sleep pattern data. The systems and methods described herein are further configured to generate the sleep pattern data by analyzing and evaluating sleep data collected from a user computing device, such as a fitness wearable device (e.g., Fitbit® brand products, Jawbone® brand products, Garmin® brand products, or any other fitness wearable; Fitbit is a registered trademark of Fitbit, Inc., San Francisco, Calif.; Jawbone is a registered trademark of AliphCom, San Francisco, Calif.; Garmin is registered trademark of Garmin Ltd., Camana Bay, Cayman Islands), a web-based phone (e.g., a "smartphone"), a personal digital assistant (PDA), a "smart watch," any other wearable device, or other web-connectable device capable of monitoring the sleep pattern of a user. Further, these systems and methods may detect in real-time that the user is asleep and/or may use the developed sleep profile of the user to determine that the user is likely asleep. These systems and methods may also use the sleep pattern data when scoring a card-present or a CNP transaction for fraud purposes, the thought being that if the legitimate cardholder is typically asleep or is known to be asleep at the time a transaction is initiated, then it is likely that the legitimate cardholder is not initiating the transaction. Thus, the transaction should be flagged as being potentially fraudulent.

In the example embodiment, a sleep pattern analyzer (SPA) system is a distributed computer network system that includes a sleep pattern analyzer (SPA) computing device. The SPA computing device includes at least one processor and at least one memory device communicatively coupled to the processor. The memory device stores computer instructions that, when executed by the processor, cause the processor to function as described herein. The SPA system further includes a sleep pattern (SP) database and an account breach (AB) database communicatively coupled to the SPA computing device. The SP database and the AB database are separate from each other, and in at least some embodiments, the SP and AB databases are in communication with the SPA computing device over different communication networks in a distributed architecture. The SP and AB databases are configured to store data associated with users' payment accounts. The payment accounts may be susceptible to an increased chance of fraud, such as payment accounts associated with lost or stolen payment cards, payment accounts involved in data breaches, payment accounts used in locations distant from locations where the users regularly uses such payment accounts, or payment accounts used at times of the day when users are usually sleeping. The data stored by the SP and AB databases may include, but is not limited to, breach data, sleep data, and sleep pattern data associated with each user of the payment accounts. The breach data, sleep data, and sleep pattern data may include, but are not limited to, a user account identifier (e.g., a payment account number (PAN)), a user computing device identifier, location data of transactions associated with the payment accounts, a transaction timestamp, a reason code indicating why the payment accounts have been identified as compromised, time when the user falls asleep, a time period when the user is asleep, a time when the user wakes up, a geolocation where the user sleeps, and/or other information associated with the user's sleep pattern and the user's payment account.

The SPA computing device is further in communication with one or more issuers and/or other third parties, such as a processor administrator associated with a payment network. The issuers are banks or other financial institutions that provide payment accounts and payment cards to users. The issuers and/or other parties submit data associated with the payment accounts to the SPA computing device to provide merchants or others issuers with the data. In some embodiments, the SPA computing device is communicatively coupled to a payment processor of a payment network, to receive the data. The payment network is a closed or private network (e.g., accessing the network requires permission from an administrator of the payment network) that has specific message protocols for transmitting and receiving messages associated with payment transactions. Various parties associated with these transactions, such as, but not limited to, merchants, banks, other financial institutions, and/or other third parties, access the payment network to process the transactions. The payment processor is configured to facilitate the communication between the parties and resolve the transactions by receiving, transmitting, and/or generating messages associated with the transactions. In the example embodiment, the SPA computing device is communicatively coupled to the SP and AB databases via one or more communication networks separate from the payment network.

The SPA computing device is also in communication with at least one user computing device, such as a fitness wearable device (e.g., Fitbit® brand products, Jawbone® brand products, Garmin® brand products, or any other fitness wearable; Fitbit is a registered trademark of Fitbit, Inc., San Francisco, Calif.; Jawbone is a registered trademark of AliphCom, San Francisco, Calif.; Garmin is registered trademark of Garmin Ltd., Camana Bay, Cayman Islands), a web-based phone (e.g., a "smartphone"), a personal digital assistant (PDA), a "smart watch," any other wearable device, or other web-connectable device capable of monitoring the sleep pattern of a user.

In some embodiments, the sleep data and/or transaction data are anonymized and aggregated (e.g., by a merchant computing device) prior to receipt by the SPA computing device (i.e., no personally identifiable information (PII) is received by the SPA computing device). In other embodiments, the SPA computing device may be configured to receive the sleep data and/or transaction data that is not yet anonymized and/or aggregated, and thus may be configured to anonymize and aggregate the sleep data and/or transaction data. In such embodiments, any PII received by the SPA computing device is received and processed in an encrypted format, or is received with the consent of individuals with which the PII is associated. In situations in which the systems discussed herein collect personal information about individuals including users and/or merchants, or may make use of such personal information, individuals may be provided with an opportunity to control whether such information is collected or to control whether and/or how such information is used. In addition, certain data may be processed in one or more ways before it is stored or used, so that personally identifiable information is removed.

In the example embodiment, the SPA computing device is configured to provide a sleep pattern (SP) service to one or more users, one or more merchants, one or more issuers, or one or more third parties that require identifying whether a payment transaction is potentially fraudulent (e.g., third parties registered to the SP service). In some embodiments, a user may use an electronic application, such as a digital wallet, to transmit to the SPA computing device a specific configuration for a user profile stored in the SPA computing device. The SPA computing device receives and stores the specific configurations. Based on these configurations, the SPA computing device generates and stores rules that the SPA computing device applies to the user profile, and then the SPA computing device updates the user profile. For example, the user may designate that the only transactions that can be authorized for a specific payment account must be initiated with a specific type of merchant (e.g., car dealerships, restaurants, grocery stores, or other type of merchant).

The user may also adjust the user profile settings by having the SPA computing device store a rule that declines transactions when the SPA computing device determines that the user (e.g., actual cardholder) is asleep or is likely asleep based on the generated sleep pattern data. The user may further adjust the user profile settings by having the SPA computing device store a rule that limits the spending amount and/or geolocations where transactions may be initiated when the sleep data for the user indicates that the user is asleep or the sleep pattern data indicates that the user would be asleep. The user may also adjust the profile settings by having the SPA computing device store a rule that determines a predefined distance from the geolocation where the user resides (e.g., location where the user usually sleeps) and the geolocation where transactions may be authorized. The user may also adjust the user profile settings by having the SPA computing device store a rule that authorizes transactions in specific locations. For example, the user may adjust the user profile settings when the user knows that he or she will travel and/or when the user is traveling, and thus the user is going to sleep in a different location from the location the user regularly sleeps in.

The SP service facilitates identification of fraudulent transactions based on the sleep pattern data of users registered with the service. The SP service may provide this information to users, merchants, issuers or any other party registered to the SP service to enable these parties to proactively identify potential fraud. Parties use the SP service using a computing device that is in communication with the SPA computing device. In some embodiments, a merchant computing device, a user computing device, and an issuer computing device may be directly in communication with the SPA computing device. In other embodiments, the merchant computing device, the user computing device, and the issuer computing device may be in communication with the SPA computing device via a payment processor of a payment network.

In the example embodiment, when the user enrolls in the SP service, the user computing device transmits to the SPA computing device user identifier data, which includes the user account identifier and the user computing device identifier. The SPA computing device stores the user identifier data in the SP database. This exchange of identifying data allows the user computing device to securely communicate with the SPA computing device and transmit the sleep data to the SPA computing device. Once the user logs into the SP service (e.g., an electronic application), the user computing device is able to securely transmit sleep data to the SPA computing device. In the example embodiment, the SPA computing device stores the sleep data in the SP database. In some embodiments, when the user enrolls in the SP service, the user provides to the SPA computing device, via the user computing device, the user's location of residence (e.g., city, state, and/or country), account identifier (e.g., PAN), and/or other information related to the user. In other embodiments, when the user enrolls in the SP service, the user only provides the account identifier, so the user computing device transmits to the SPA computing device the account identifier and user computing device identifier. In this case, the SPA computing device receives additional data associated with the user when the SPA computing device receives sleep data, breach data, and/or transaction data associated with the user account identifier.

In the example embodiment, the user computing device collects the sleep data when the user falls asleep, while the user is asleep, and when the user wakes up. In some embodiments, the SPA computing device receives the sleep data immediately after the user computing device collects such data. In other embodiments, the SPA computing device receives the sleep data at a later time. For example, the user computing device may temporarily not be connected to the SPA computing device due to a lost connection or other reason that disables communication between the user computing device and the SPA computing device. Once the user computing device establishes communication with the SPA computing device, the user computing device transmits the sleep data, which is then received by the SPA computing device. For example, the user may be traveling to a geographical location outside the user's typical location (e.g., foreign countries) and the user computing device may lose connectivity with the SPA computing device while the user is traveling to the user's destination. If the user sleeps on the way to the destination and the user computing device is not connected to the SPA computing device, the user computing device collects the sleep data if the user falls asleep and transmits the sleep data to the SPA computing device one the connection is re-established between both devices. The SPA computing device may transmit a notification to an issuer once the SPA computing device detects that the user is going to a geographical location outside the user's typical location. Thus, the issuer may authorize a transaction initiated by the user at the user's destination without requiring additional verification from the user.

In the example embodiment, the SPA computing device is configured to parse the stored user identifier data to match such data to the sleep data. More specifically, in some embodiments, the SPA computing device may match the user account identifier included in the received sleep data to the user account identifier stored in the SP database. In other embodiments, the SPA computing device may match the user computing device identifier included in the received sleep data to the user computing device identifier stored in the SP database. Once the stored user identifier data and the sleep data are matched, the SPA computing device associates the sleep data to the stored user identifier data and stores the sleep data within the SP database. The SPA computing device is further configured to generate sleep pattern data. The sleep pattern data includes, but is not limited to, a user sleep time, a geolocation where the user usually sleeps based on historical sleep data collected by the SPA computing device, and one or more user computing devices that are usually used by the user to initiate transactions user geolocation based on historical sleep data collected by the SPA computing device.

The SPA computing device is configured to determine the user sleep time. In certain embodiments, the SPA computing device may determine the user sleep time by calculating an average of the time when the user falls asleep and an average of the time when the user wakes up, and determining the delta between both averages. For example, if the average of the time when the user falls asleep is 10:33 p.m. and the average of the time when the user wakes up is 5:42 a.m., the user sleep time is 10:33 p.m. to 5:42 p.m. In alternative embodiments, the SPA computing device may receive from the user computing device sleep data that includes the time period when the user is asleep. In this case, the SPA computing device may determine the user sleep time by calculating an average of the time period when the user is asleep. In other embodiment, the SPA computing device may determine the user sleep time by calculating a distribution of the user sleep time received and identify the mode in the distribution. By determining the user sleep time, the SPA computing device may flag any received transaction associated with the user during such time, as explained in more detail below.

In other embodiments, the SPA computing device applies the best sleep effort (BES) model to determine the user sleep time. The BES model uses a sensor-based algorithm that predicts the duration of the user sleep time. The BES model is based on a linear combination of phone usage, accelerometer, audio, light, and time features using a stored sleep pattern data.

The SPA computing device is configured to collect and store sleep data associated with a user of a payment account. In the example embodiment, the user computing device monitors the sleep pattern of the user while the user is asleep. The user computing device is configured to collect the sleep data, which includes, but is not limited to, a time when the user falls asleep, a time period when the user is asleep, a time when the user wakes up, a geolocation where the user sleeps, a user account identifier, a user computing device identifier, and other related data to the user and the sleep pattern of the user. The user computing device is also configured to determine in real-time when the user is asleep. The user computing device is further configured to use an electronic application installed into the user computing device to transmit data to the SPA computing device.

In some embodiments, the user computing device is further configured to transmit to the SPA computing device sleep data indicating that the user is asleep. The SPA computing device may update the status (e.g., indicate that the user is asleep) of one or more account identifiers associated with the sleep data corresponding to the user who is asleep. In one example, if the SPA computing device receives transaction data indicating that a payment transaction has been initiated for the one or more account identifiers, the SPA computing device may flag the one or more account identifiers and transmit a message, such as an alert message, to the issuer indicating that the user associated with the one or more account identifiers is asleep and the payment transaction may be fraudulent. In yet another example, even if the SPA computing device has indicated that the user associated with the one or more account identifiers is asleep, the SPA computing device may not flag the one or more accounts.

In some embodiments, the SPA computing device is configured to request the user computing device to verify whether the user is asleep. If the SPA computing device has not receive sleep data from the user computing device during a predefined time period, the SPA computing device may request the user computing device to transmit the sleep data. The predefined time period may be determined by a user input setting. The predefined time period may also be determined by the SPA computing device. The SPA computing device may store a time when the SPA computing device starts receiving the sleep data from the user computing device and calculate an average of the time when sleep data starts to be received. The SPA computing device may compare the calculated average time when the sleep data starts to be received and a predefined tolerance time period (e.g., a predefined time that the SPA computing device waits after the sleep data has not been received and before the SPA computing device transmits the request to the user computing device). After making the comparison, the SPA computing device determines whether the sleep data has not been received after the predefined tolerance time period. For example, the SPA computing device may determine that the average time when the sleep data is received is 11:05 p.m. and the predefined tolerance time is 3 hours. If the SPA computing device has not received the sleep data by 2:05 a.m., the SPA computing device will send the request to the user computing device. Once the SPA computing device receives the sleep data, the SPA computing device may determine whether the user is asleep. If the SPA computing device determines that the user should be asleep and the SPA computing device receives transaction data associated with a payment transaction of the user account identifier during the time that the user should be asleep, the SPA computing device may flag the transaction data and may transmit to the user, issuer, merchants, and/or any other party registered to the SP service a message indicating that the payment transaction may be fraudulent.

In certain embodiments, the SPA may not flag the one or more account identifiers when the transaction is an account-on file transaction. As used herein, an "account-on-file" transaction is a transaction in which the merchant retrieves stored payment information for a repeat customer, thereby eliminating the requirement of the customer re-entering his or her payment information for subsequent purchases. In one example, the account-on-file transaction may be a subscription service that periodically charges the customer for the service. In another example, the account-on-file transaction may be a transaction initiated via a merchant website by a customer having a stored profile with the merchant. The merchant may also store other information for each user, such as contact information, shopping behavior, and the like. In other embodiments, the SPA computing device may not flag the one or more account identifiers if the user has setup settings transmitted to the SPA computing device that enable transactions to be approved even if the SPA computing device identifies that the user is asleep.

In the example embodiment, the SPA computing device is configured to collect geolocation data of transactions associated with the user payment account, a transaction timestamp, and/or a reason code indicating why the payment accounts have been identified as compromised. The SPA computing device is also configured to store the geolocation data of transactions associated with the user payment account, the transaction timestamp, and/or the reason code indicating why the payment accounts have been identified as compromised in the AB database.

In the example embodiment, the SPA computing device is configured to compare the data stored in the AB database to the data stored in the SP database. For example, the SPA computing device may compare the transaction time stamp to the user sleep time. In certain embodiments, if the transaction time stamp falls within the user sleep time, the SPA computing device may flag the transaction as potentially fraudulent and/or may further decline a transaction. In alternative embodiments, if the transaction time stamp falls within the user sleep time, the SPA computing device may flag the transaction as compromised and may further parse the SP database to lookup for the geolocation where the user generally sleeps (e.g., the geolocation that is the mode of a distribution of the stored geolocation, where the distribution is calculated by the SPA computing device). For example, if the geolocation where the user sleeps is frequently located in Chicago, Ill., which time is UTC/GMT −6 hours (Central Standard Time), but the last entry of the geolocation where the user slept is Reykjavik, Iceland, which time is UTC/GMT Greenwich Mean Time, the SPA computing device may identify that the user is in Reykjavik and approve a transaction if the time in Reykjavik does not fall within the user sleep time. In the example embodiment, the SPA computing device is configured to notify the user, the merchant, and/or the issuer when the SPA computing device detects a fraudulent transaction. For example, the SPA computing device may transmit to the user computing device a notification that a transaction may be fraudulent while the user is asleep. The user computing device, which is synced with an electronic application, such as a digital wallet, uses the electronic application to receive the notification. When the user wakes up, the user may see the transaction attempt and denial.

The AB database is configured to store breach data associated with payment accounts potentially involved in data breaches (also known as "account data compromises") involving payment information. A data breach occurs when a fraudulent party gains access to payment account information by using a stolen or lost payment card, or gaining access to a computing device and/or a database storing the payment account information. The payment account information may be used to complete fraudulent purchases. In one example, the payment account information may be collected from a computing device associated with a single account holder (e.g., a cardholder). In another example, the payment account information may be collected from a stolen or lost payment cards. In yet another example, a merchant that stores payment account information for account-on-file transactions may experience a data breach by a fraudulent party to retrieve the payment account information. As used herein, an "account-on-file" transaction is a transaction in which the merchant retrieves stored payment information for a repeat customer, thereby eliminating the requirement of the customer re-entering his or her payment information for subsequent purchases. In one example, the account-on-file transaction may be a subscription service that periodically charges the customer for the service. In another example, the account-on-file transaction may be a transaction initiated via a merchant website by a customer having a stored profile with the merchant. The merchant may also store other information for each user, such as contact information, shopping behavior, and the like.

The AB database enables other parties (e.g., other merchants and banks) to access the breach data to prevent or otherwise limit fraudulent activity as a result of the data breach. In the example embodiment, the AB database receives the breach data from the SPA computing device after the SPA computing device has determined that a fraudulent transaction has occurred, as explained above. In one embodiment, the breached or compromised party transmits the breach data to the AB database directly. In other embodiments, the breach data is sent indirectly to the AB database. For example, the breach data may be transmitted to the AB database via the payment processor.

The breach data may include, but is not limited to, an account identifier, a reason code, and a timestamp for each potentially compromised payment account. The reasons code may indicate a potential origin of the data breach and/or how the potential breach was detected. The timestamp may indicate an estimated time the breach occurred, when the payment account data breach was detected, and/or when the breach was reported to the AB database. In other embodiments, the breach data includes additional, fewer, or alternative data elements, including those described elsewhere herein. The breach data may be stored by the AB database for a predetermined time period to facilitate storage capacity management.

In some embodiments, the SPA computing device is also in communication with a historical authorization (HA) database. The HA database is configured to store historical transaction data of historical transactions. The transaction data may be received from the payment processor and/or other computing devices within the payment network. The transaction data includes data elements retrieved and/or generated for one or more transactions processed by the payment network. The transaction data may include, but is not limited to, an account identifier, a timestamp (e.g., date and time), a merchant identifier, a payment amount, a payment method (e.g., card-not-present, account-on-file, etc.), a geolocation identifier, product(s) purchased, and/or other transaction-related data elements for each transaction associated with the transaction data.

The transaction data is stored in the HA database as a plurality of historical authorization messages. The historical authorization messages are messages formatted based on protocols of the payment network and are used to confirm authorization of a transaction. That is, the transactions associated with the historical authorization messages are transactions that have been previously authorized. In one example, the authorization messages include ISO® 8583 compliant messages and ISO® 20022 compliant messages. As used herein, "ISO®" refers to a series of standards approved by the International Organization for Standardization (ISO is a registered trademark of the International Organization for Standardization of Geneva, Switzerland). ISO® 8583 compliant messages are defined by the ISO® 8583 standard which governs financial transaction card originated messages and further defines acceptable message types, data elements, and code values associated with such financial transaction card originated messages. ISO® 8583 compliant messages include a plurality of specified locations for data elements. ISO® 20022 compliant messages are defined by the ISO® 20022 standard. For example, ISO® 20022 compliant messages may include acceptor to issuer card messages (ATICA).

In at least some embodiments, each historical authorization message is associated with one respective transaction.

In other embodiments, the authorization message may be a batch message associated with a plurality of transactions. In the example embodiment, the HA database is configured to be searched, sorted, and/or otherwise organized using the data elements of the historical authorization messages. For example, the historical authorization messages may be filtered to only show transaction associated with a particular merchant or a particular merchant location. In at least some embodiments, the historical authorization messages are stored by the HA database for a predetermined time period.

The SPA computing device is configured to calculate a fraud score for each user account identifier. The SPA computing device may use the transaction data stored in the HA database, breach data stored in the AB database, and the sleep data stored in the SP database to calculate the fraud score. The SPA computing device may retrieve the transaction data, the breach data, sleep data, and the sleep pattern data to calculate the fraud score. The SPA computing device may use predefined thresholds and algorithms to calculate the fraud score. The SPA computing device may transmit the retrieved transaction data, breach data, and/or sleep pattern data to an issuer, so the issuer may calculate the fraud score.

The SPA computing device is further configured to build a sleep profile table for users of the SP service. The SPA computing device may use the data stored in the SP, AB, and HA databases to build the sleep profile table. In some embodiments, the SPA computing device uses the sleep profile table to calculate the fraud score. For example, the SPA computing device may compare data in the sleep profile table to transaction data in order to identify fraudulent activity. The SPA computing device may also use the sleep profile table for other purposes, such as the creation of reports, the issuance of notifications for parties registered with the SP service, or other suitable uses that the sleep profile table may provide.

At least one technical problem with known systems is that, in view of the volume of financial transactions and the diversity of preferences between cardholders, it can be difficult, time-consuming, and/or resource-intensive to determine whether a financial transaction is fraudulent. To reduce a risk of fraudulent transactions, at least some known systems are configured to decline a financial transaction if the cardholder does not provide authentication in association with the financial transaction. The embodiments described herein address at least these technical problems. By processing financial transactions in the manner described in this disclosure, some embodiments improve user experience, user efficiency, and/or user interaction performance by using transaction data associated with a prior financial transaction to calculate risk associated with approving a request for authorization for a present financial transaction. Additionally or alternatively, some embodiments potentially reduce a quantity of requests to provide authentication. In this manner, the embodiments described herein may facilitate achieving a balance between convenience to a user (e.g., actual cardholder) and security against fraudulent transactions. Additionally, some embodiments may reduce processor load by reducing an amount of data to be analyzed or processed, reduce network bandwidth usage, and/or improve communication between systems by reducing an amount of data to be transmitted, improve processor security and/or data transmission security by using biometric data to process financial transactions, and/or reduce error rate by automating the analysis and processing of financial transactions. In some embodiments, the subject matter described herein may facilitate increasing processor speed and/or improving operating system resource allocation.

The methods and systems described herein may be implemented using computer programming or engineering techniques including computer software, firmware, hardware or any combination or subset thereof, wherein the technical effects may be achieved by performing one of the following steps: (a) receiving sleep data that includes at least a user account identifier, a first timestamp, and a first geolocation; (b) storing the sleep data in a sleep pattern (SP) database; (c) generating sleep pattern data using the sleep data, wherein generating the sleep pattern data includes calculating a distribution of the first timestamp and a distribution of the first geolocation; (d) receiving transaction data that includes at least the user account identifier, a second timestamp, a merchant identifier, and a second geolocation; (e) parsing the SP database using the user account identifier; (f) correlating the second timestamp to the first timestamp and the first geolocation to the second geolocation; (g) determining the second timestamp falls within a predefined time period of the sleep pattern data and the second geolocation is within a predefined distance from the first geolocation; (h) generating a fraudulent notification that includes the user account identifier, the second timestamp, the merchant identifier, and the second geolocation; and (i) transmitting the fraudulent notification to at least one of an issuer, a merchant associated with the merchant identifier, and a user associated with the user account identifier.

Described herein are computer systems such as a payment processor and a SPA computing device. As described herein, all such computer systems include a processor and a memory.

Further, any processor in a computer device referred to herein may also refer to one or more processors wherein the processor may be in one computing device or a plurality of computing devices acting in parallel. Additionally, any memory in a computer device referred to herein may also refer to one or more memories wherein the memories may be in one computing device or a plurality of computing devices acting in parallel.

As used herein, a processor may include any programmable system including systems using micro-controllers, reduced instruction set circuits (RISC), application specific integrated circuits (ASICs), logic circuits, and any other circuit or processor capable of executing the functions described herein. The above examples are example only, and are thus not intended to limit in any way the definition and/or meaning of the term "processor."

As used herein, the term "database" may refer to either a body of data, a relational database management system (RDBMS), or to both. As used herein, a database may include any collection of data including hierarchical databases, relational databases, flat file databases, object-relational databases, object oriented databases, and any other structured collection of records or data that is stored in a computer system. The above examples are example only, and thus are not intended to limit in any way the definition and/or meaning of the term database. Examples of RDBMS's include, but are not limited to including, Oracle® Database, MySQL, IBM® DB2, Microsoft® SQL Server, Sybase®, and PostgreSQL. However, any database may be used that enables the systems and methods described herein. (Oracle is a registered trademark of Oracle Corporation, Redwood Shores, Calif.; IBM is a registered trademark of International Business Machines Corporation, Armonk, N.Y.; Microsoft is a registered trademark of Microsoft Corporation, Redmond, Wash.; and Sybase is a registered trademark of Sybase, Dublin, Calif.)

In one embodiment, a computer program is provided, and the program is embodied on a computer readable medium. In an example embodiment, the system is executed on a single computer system, without requiring a connection to a sever computer. In a further embodiment, the system is being run in a Windows® environment (Windows is a registered trademark of Microsoft Corporation, Redmond, Wash.). In yet another embodiment, the system is run on a mainframe environment and a UNIX® server environment (UNIX is a registered trademark of X/Open Company Limited located in Reading, Berkshire, United Kingdom). The application is flexible and designed to run in various different environments without compromising any major functionality. In some embodiments, the system includes multiple components distributed among a plurality of computing devices. One or more components may be in the form of computer-executable instructions embodied in a computer-readable medium.

As used herein, an element or step recited in the singular and proceeded with the word "a" or "an" should be understood as not excluding plural elements or steps, unless such exclusion is explicitly recited. Furthermore, references to "example embodiment" or "one embodiment" of the present disclosure are not intended to be interpreted as excluding the existence of additional embodiments that also incorporate the recited features.

As used herein, the terms "software" and "firmware" are interchangeable, and include any computer program stored in memory for execution by a processor, including RAM memory, ROM memory, EPROM memory, EEPROM memory, and non-volatile RAM (NVRAM) memory. The above memory types are example only, and are thus not limiting as to the types of memory usable for storage of a computer program.

The systems and processes are not limited to the specific embodiments described herein. In addition, components of each system and each process can be practiced independent and separate from other components and processes described herein. Each component and process also can be used in combination with other assembly packages and processes.

As used herein, the terms "transaction card," "financial transaction card," and "payment card" refer to any suitable transaction card, such as a credit card, a debit card, a prepaid card, a charge card, a membership card, a promotional card, a frequent flyer card, an identification card, a gift card, and/or any other device that may hold payment account information, such as mobile phones, smartphones, personal digital assistants (PDAs), key fobs, and/or computers. Each type of transaction card can be used as a method of payment for performing a transaction.

The following detailed description illustrates embodiments of the disclosure by way of example and not by way of limitation. It is contemplated that the disclosure has general application to identify fraudulent activity using sleep pattern data associated with a user.

FIG. 1 is a schematic diagram illustrating an example multi-party payment card processing system 120 for enabling payment-by-card transactions between merchants 124, users 122, and issuer bank 130. Embodiments described herein may relate to a transaction card system, such as a credit card payment system using the Mastercard® payment card system payment network 128 (also referred to as an "interchange" or "interchange network"). The Mastercard® payment card system payment network 128 is a set of proprietary communications standards promulgated by Mastercard International Incorporated® for the exchange of financial transaction data and the settlement of funds between financial institutions that are registered with Mastercard International Incorporated®. (Mastercard is a registered trademark of Mastercard International Incorporated located in Purchase, N.Y.).

In payment card processing system 120, a financial institution, such as issuer bank 130, issues a transaction card or electronic payments account identifier, such as a credit card or debit card, to a user or user 122, who uses the transaction card to tender payment for a purchase from a merchant 124. To accept payment with the transaction card, merchant 124 must normally establish an account with a financial institution that is part of the financial payment system. This financial institution is usually called the "merchant bank," the "acquiring bank," or the "acquirer." When user 122 tenders payment for a purchase with a transaction card, merchant 124 requests authorization from a merchant bank 126 for the amount of the purchase. The request may be performed over the telephone, but is usually performed through the use of a point-of-sale terminal, which reads user's 122 account information from a magnetic stripe, a chip, or embossed characters on the transaction card and communicates electronically with the transaction processing computers of merchant bank 126. Alternatively, merchant bank 126 may authorize a third party to perform transaction processing on its behalf. In this case, the point-of-sale terminal will be configured to communicate with the third party. Such a third party is usually called a "merchant processor," an "acquiring processor," or a "third party processor."

Using an interchange network 128, computers of merchant bank 126 or merchant processor will communicate with computers of an issuer bank 130 to determine whether user account 132 associated with user 122 is in good standing and whether the purchase is covered by user's 122 available credit line. Based on these determinations, the request for authorization will be declined or accepted. If the request is accepted, an authorization code is issued to merchant 124.

In the example embodiment, user 122 provides user account data, such as a biometric sample or other type of user identifier (e.g., username and password). During authorization, one or more parties to the transaction, such as interchange network 128, may communicate with a sleep pattern analyzer (SPA) system 100 that is configured to identify fraudulent activity using sleep pattern data associated with user 122. In the example embodiment, SPA system 100 detects fraudulent activity based on user 122 sleep pattern data and transaction data (which includes account data) for payment transactions. During operation, interchange network 128 may transmit sleep pattern data and transaction data to SPA system 100, and SPA system may transmit one or more messages to interchange network 128 that may include one or more indicators that a transaction may be fraudulent.

When a request for authorization is accepted, the available credit line of user account 132 is decreased. Normally, a charge for a payment card transaction is not posted immediately to user account 132 because bankcard associations, such as Mastercard International Incorporated®, have promulgated rules that do not allow merchant 124 to charge, or "capture," a transaction until goods are shipped or services are delivered. However, with respect to at least some debit card transactions, a charge may be posted at the time of the transaction. When merchant 124 ships or delivers the goods or services, merchant 124 captures the transaction by, for example, appropriate data entry procedures on the point-ofsale terminal. This may include bundling of approved transactions daily for standard retail purchases. If user 122 cancels a transaction before it is captured, a "void" is generated. If user 122 returns goods after the transaction has been captured, a "credit" is generated. Interchange network 128 and/or issuer bank 130 stores the transaction card information, such as a category of merchant, a merchant identifier, a geolocation where the transaction was completed, amount of purchase, date and time of transaction, in a database (not shown). SPA system 100 may also store the transaction card information in one or more databases, such as, SP database 204, AB database 206, and HA database 208 (shown in FIG. 2).

After a purchase has been made, a clearing process occurs to transfer additional transaction data related to the purchase among the parties to the transaction, such as merchant bank 126, interchange network 128, and issuer bank 130. More specifically, during and/or after the clearing process, additional data, such as a time of purchase, a merchant name, a type of merchant, purchase information, user account information, a type of transaction, itinerary information, information regarding the purchased item and/or service, and/or other suitable information, is associated with a transaction and transmitted between parties to the transaction as transaction data, and may be stored by any of the parties to the transaction. In the example embodiment, when user 122 purchases travel, such as airfare, a hotel stay, and/or a rental car, at least partial itinerary information is transmitted during the clearance process as transaction data. When interchange network 128 receives the itinerary information, interchange network 128 routes the itinerary information to a database, such as HA database 208.

For debit card transactions, when a request for a personal identification number (PIN) authorization is approved by the issuer, user account 132 is decreased. Normally, a charge is posted immediately to user account 132. The payment card association then transmits the approval to the acquiring processor for distribution of goods/services or information, or cash in the case of an automated teller machine (ATM).

After a transaction is authorized and cleared, the transaction is settled among merchant 124, merchant bank 126, and issuer bank 130. Settlement refers to the transfer of financial data or funds among merchant's 124 account, merchant bank 126, and issuer bank 130 related to the transaction. Usually, transactions are captured and accumulated into a "batch," which is settled as a group. More specifically, a transaction is typically settled between issuer bank 130 and interchange network 128, and then between interchange network 128 and merchant bank 126, and then between merchant bank 126 and merchant 124.

In some embodiments, user 122 registers one or more payment cards with a digital wallet. Having done this, user 122 can interact with a participating online merchant 124. At the check-out stage, online merchant 124 displays a button on the merchant website which user 122 can click on in order to make a payment using the user's digital wallet. Online merchant 124 then redirects the user to a "switch" operated by interchange network 128. Using a cookie located on the user's computer, the "switch" is able to determine which wallet-hosting server (also referred herein to as "wallet-hosting system) hosts a wallet associated with user 122. The switch then establishes a connection between the user's computer and the appropriate wallet-hosting system, which presents user 122 with a sign-in page (e.g., as a pop-up window), where there is an authentication process (e.g., entry of a pre-agreed password). This log-in process may use the same login credentials (e.g., password) which the user also uses to obtain access to other online banking activities.

The wallet-hosting system then securely transfers the user's payment information to the online merchant's domain. The merchant's domain submits the user's payment information to merchant bank 126 for a separate authorization process in which the acquiring domain communicates with the issuer bank 130 to ask the bank to authorize the transaction. Thus, user 122 is not required to enter their card details (except at the stage of initially registering with the wallet-hosting system), and the online transaction process is streamlined with only a single redirection, and consistent branding for the entire payment process, irrespective of the online merchant 124.

In some embodiments, a unique identifier is provided to user 122. The unique identifier is different from the user's account number. In these embodiments, interchange network 128 stores the unique identifier in a database, such as HA database 208, along with user account 132. When interchange network 128 receives the unique identifier, interchange network 128 determines the associated user account 132 and uses that information in processing the payment transaction.

Figure 2:
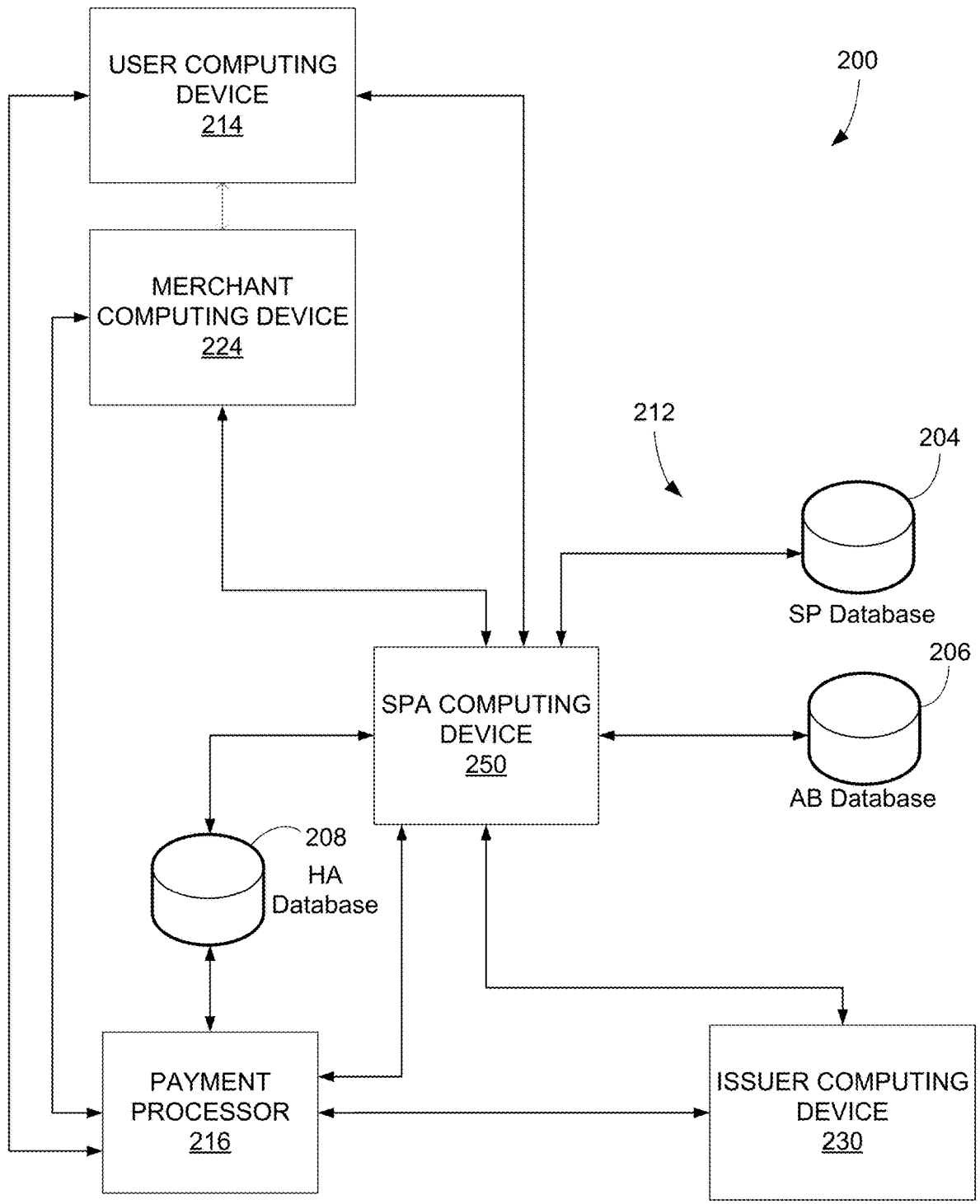

FIG. 2 is a simplified block diagram of an example sleep pattern analyzer (SPA) system 200, similar to SPA system 100 (shown in FIG. 1), in which a variety of computing devices are communicatively coupled to each other via a plurality of network connections. These network connections may be the Internet, a local area network (LAN), a wide area network (WAN), or other connections capable of transmitting data across computing devices. SPA system 200 includes at least one sleep pattern analyzer (SPA) computing device 250, sleep pattern (SP) database 204, account breach (AB) database 206, and historical authorization (HA) database 208. In one embodiment, SPA computing device, SP database 204, AB database 206, and HA database 208 are components of server system 212. Server system 212 may be a server, a network of multiple computer devices, a virtual computing device, or the like. SPA computing device 250 is connected to at least one merchant computing device 224 associated with merchant 124 (shown in FIG. 1), user computing device 214 associated with user 122 (shown in FIG. 1), and an issuer computing device 230 associated with issuer bank 130 (shown in FIG. 1) via at least a payment processor 216 of the interchange network 128 (shown in FIG. 1). SPA computing device 250 may be directly communicatively coupled to merchant computing device 224, user computing device 214, issuer computing device 230, payment processor 216, SP database 204, AB database 206, and HA database 208 via one or more communication networks or communication channels.

In some embodiments, server system 212 includes a database server (not shown) that is connected to SP database 204, AB database 206, and HA database 208, which contain information on a variety of matters, as described below in greater detail. In one embodiment, SP database 204, AB database 206, and/or HA database 208 are stored in server system 212 and can be accessed by potential users of server system 212. In an alternative embodiment, SP database 204, AB database 206, and/or HA database 208 are stored remotely from server system 212 and may be non-centralized. Each SP database 204, AB database 206, and HA database 208 may include single databases having separated sections or partitions or may include multiple databases, each being separate from each other.

In certain embodiments, SPA computing device 250 is communicatively coupled to payment processor 216. In certain embodiments, SPA computing device 250 is integrated with one or more of SP database 204, AB database 206, and/or HA database 208, and payment processor 216 such that a single computing device or distributed computing system performs the functions of each of the integrated devices as described herein.

SP database 204, AB database 206, and/or HA database 208 are communicatively coupled to SPA computing device 250 via separate communication channels and/or networks. The communication channels or networks may be separate from interchange network 128 to facilitate reduced bandwidth and processing burdens associated with the SPA service on payment processor 216 and interchange network 128. SP database 204, AB database 206, and/or HA database 208 are separate from each other to facilitate storage of different data. In at least some embodiments, SP database 204, AB database 206, and/or HA database 208 are in communication with one or more merchants, acquirers, issuers, users, and/or other parties associated with payment accounts and transactions in order to receive and store sleep data associated with user 122 and breach data associated with user account 132 (shown in FIG. 1). SP database 204, AB database 206, and/or HA database 208 may also be in communication with one or more issuers to facilitate retrieval of the data stored in SP database 204, AB database 206, and/or HA database 208 during authorization of a transaction.

In the example embodiment, SP database 204 is configured to store sleep data and sleep pattern data associated with user 122. The sleep data may include, but is not limited to, a time when user 122 falls asleep, a time period when user 122 is asleep, a time when user 122 wakes up, a geolocation where user 122 sleeps, an identifier of user account 132, an identifier of user computing device 214, and other related data to user 122 and the sleep pattern of user 122. In the example embodiment, AB database 206 is configured to store breach data. The breach data may include, but is not limited to, an identifier of user account 132 (e.g., a payment account number (PAN)), an identifier of user computing device 214, location data of transactions associated with the user account 132, a transaction timestamp, a reason code indicating why user account 132 has been identified as compromised, and/or other information associated with user 122 and user account 132. In some embodiments, SP database 204 and AB database 206 may store transaction data, such as logs, events, and metrics, associated with user account 132. SP database 204 and AB database 206 are in communication with one or more issuers to facilitate retrieval of the data stored in SP database 204 and AB database 206 during authorization of a transaction.

In the example embodiment, HA database 208 is configured to store historical authorization messages from a plurality of historical transactions. The authorization messages include data elements corresponding to a respective historical transaction, including, but not limited to, a historical account identifier (e.g., a PAN), a transaction timestamp, an account expiry date, a payment amount, a merchant identifier, and/or a user identifier. In the example embodiment, each historical authorization message is associated with a transaction that has been successfully authorized. That is, none of the authorization messages are associated with failed or declined transactions. In other embodiments, the stored historical authorization message may include one or more authorization message associated with failed or declined transactions.

In some embodiments, the sleep data and/or transaction data are anonymized and aggregated (e.g., by a merchant computing device) prior to receipt by SPA computing device 250 (i.e., no personally identifiable information (PII) is received by SPA computing device 250). In other embodiments, SPA computing device 250 may be configured to receive the sleep data and/or transaction data that is not yet anonymized and/or aggregated, and thus may be configured to anonymize and aggregate the sleep data and/or transaction data. In such embodiments, any PII received by SPA computing device 250 is received and processed in an encrypted format, or is received with the consent of individuals with which the PII is associated. In situations in which the systems discussed herein collect personal information about individuals including users 122 and/or merchants 124, or may make use of such personal information, individuals may be provided with an opportunity to control whether such information is collected or to control whether and/or how such information is used. In addition, certain data may be processed in one or more ways before it is stored or used, so that personally identifiable information is removed.

In the example embodiment, the authorization messages are generated and/or collected by payment processor 216. Payment processor 216 is configured to process transactions within interchange network 128. That is, payment processor 216 is configured to receive, process, and/or transmit transaction data, authorization messages (e.g., ISO® 8583 compliant messages and ISO® 20022 compliant messages), and other transaction-related messages within interchange network 128. Interchange network 128 is configured to facilitate processing transactions (e.g., payment card transactions) by providing particular message protocols to merchants, issuers, acquirers, and payment processor 216 to perform particular functions within interchange network 128. In the example embodiment, interchange network 128 is a closed network. That is, interchange network 128 is configured to prevent unpermitted access to the messages within interchange network 128.

At least a portion of the authorization messages processed by payment processor 216 may be stored in HA database 208. Additionally or alternatively, one or more different computing devices associated with interchange network 128 are communicatively coupled to HA database 208 to provide at least a portion of the authorization messages.

In the example embodiment, SPA computing device 250 is configured to receive transaction data from merchant computing device 224, over interchange network 128. As noted with respect to FIG. 1, when user 122 performs a transaction at a merchant location, transaction data is generated. Transaction data may be transmitted across computing devices as an authorization request message. In one embodiment, when user 122 initiates a transaction at merchant computing device 224 associated with merchant 124, transaction data for the transaction is transmitted to server system 212. Server system 212 processes the transaction data in the manner described with respect to FIG. 1 and also transmits it to SPA computing device 250.

The transaction data may include transaction amount, a transaction date, account data related to the payment card used to perform the transaction (e.g., PAN associated with payment card, card expiration date, card issuer, card security code, or the like), a merchant identifier, stock-keeping unit (SKU) data relating to the goods or services purchased from the user, or the like.

In the example embodiment, SPA computing device 250 receives an authorization request message along with transaction data (e.g., merchant information, SKU data relating to the goods or services purchased from the user, or the like). SPA computing device 250 is also configured to store transaction data in, SP database 204, AB database 206, and/or HA database 208 based on an account identifier associated with user account 132. SPA computing device 250 is further configured to receive one or more authorization request messages that may include an identifier of user computing device 214, an identifier of user account 132, and other data associated with user 122.

SPA computing device 250 is configured to collect and store sleep data associated with a user of a payment account, such as user 122. In the example embodiment, user computing device 214 monitors the sleep of user 122 while user 122 is asleep. User computing device 214 is configured to collect the sleep data, which includes, but is not limited to, a time when user 122 falls asleep, a time period when user 122 is asleep, a time when user 122 wakes up, a geolocation where user 122 sleeps, an identifier of user account 132, an identifier of user computing device 214, and other related data to user 122 and the sleep pattern of user 122. User computing device 214 is also configured to use an electronic application installed into user computing device 214 to transmit data to SPA computing device 250.

SPA computing device 250 is also configured to provide a sleep pattern (SP) service to one or more users 122, one or more merchants 124, one or more issuer banks 130, or one or more third parties that require identifying whether a payment transaction is fraudulent (e.g., third parties registered to the SP service). In some embodiments, user 122 may use an electronic application, such as a digital wallet, to transmit to SPA computing device 250 a specific configuration for a user profile stored in SPA computing device 250. SPA computing device 250 receives and stores the specific configurations. Based on these configurations, SPA computing device 250 generates and stores rules that SPA computing device 250 applies to the user profile, and then SPA computing device 250 updates the user profile. For example, user 122 may designate that the only transactions that can be authorized for a specific payment account must be initiated with a specific type of merchant (e.g., car dealerships, restaurants, grocery stores, or other type of merchant). User 122 may also adjust the user profile by having SPA computing device 250 store a rule that declines transactions when SPA computing device 250 determines that user 122 is asleep or is likely asleep based on the generated sleep pattern data. User 122 may further adjust the user profile settings by having SPA computing device 250 store a rule that limits the spending amount and/or geolocations where transactions may be initiated. User 122 may also adjust the profile settings by having SPA computing device 250 store a rule that determines a predefined distance from the geolocation where user 122 resides (e.g., user's residential zip code) and the geolocation where transactions may be authorized. User 122 may also adjust the user profile settings by having SPA computing device 250 store a rule that authorizes transactions in specific locations. For example, user 122 may adjust the user profile settings when user 122 knows that he or she will travel and/or when user 122 is traveling.

In the example embodiment, when user 122 enrolls in the SP service, user computing device 214 transmits to SPA computing device 250 user identifier data, which includes at least an identifier of user account 132 and an identifier of user computing device 214. SPA computing device 250 stores the user identifier data in SP database 204. Once user 122 has logged onto the electronic application, user computing device 214 is enabled to transmit sleep data to SPA computing device 250. In the example embodiment, SPA computing device 250 stores the sleep data and sleep pattern data in SP database 204.

In the example embodiment, user computing device 214 collects the sleep data when user 122 falls asleep, while user 122 is asleep, and when user 122 wakes up. In some embodiments, SPA computing device 250 receives the sleep data immediately after user computing device 214 collects such data. In other embodiments, SPA computing device 250 receives the sleep data at a later time. For example, user computing device 214 may temporarily not be connected to SPA computing device 250 due to lost connection or other reason that disables communication between user computing device 214 and SPA computing device 250. Once user computing device 214 establishes communication with SPA computing device 250, user computing device 214 transmits the sleep data, which is then received by SPA computing device 250.

SPA computing device 250 is further configured to parse the stored user identifier data to match such data to the sleep data. More specifically, in some embodiments, SPA computing device 250 may match the identifier of user account 132 included in the received sleep data to the identifier of user account 132 stored in the SP database. In other embodiments, SPA computing device may match the identifier of user computing device 214 included in the received sleep data to the identifier of user computing device 214 stored in the SP database. Once the stored user identifier data and the sleep data are matched, the SPA computing device associates the sleep data to the stored user identifier data and stores the sleep data within SP database 204. SPA computing device 250 is further configured to determine a sleep time of user 122. In certain embodiments, SPA computing device 250 may determine the sleep time of user 122 by calculating an average of the time when user 122 falls asleep and an average of the time when user 122 wakes up, and determining the delta between both averages. For example, if the average of the time when user 122 falls asleep is 10:33 pm and the average of the time when user 122 wakes up is 5:42 am, the sleep time of user 122 is 10:33 pm to 5:42 pm. In alternative embodiments, SPA computing device 250 may receive from the user computing sleep data that includes the time period when user 122 is asleep. In this case, SPA computing device 250 may determine the sleep time of user 122 by calculating an average of the time period when user 122 is asleep. By determining the sleep time of user 122, SPA computing device 250 may flag any received transaction associated with user 122 during such time.

In the example embodiment, SPA computing device 250 is configured to collect location data of transactions associated with user account 132, a transaction timestamp, and/or a reason code indicating why the payment account has been identified as compromised. SPA computing device 250 is also configured to store the location data of transactions associated with user account 132, the transaction timestamp, and/or the reason code indicating why the payment account has been identified as compromised in AB database 206.

SPA computing device 250 is also configured to compare the data stored in AB database 206 to the data stored in SP database 204. For example, SPA computing device 250 may compare the transaction time stamp to the sleep time of user 122. In certain embodiments, if the transaction time stamp falls within the sleep time of user 122, SPA computing device 250 may flag the transaction as fraudulent and may further decline a transaction. In alternative embodiments, if the transaction time stamp falls within the sleep time of user 122, SPA computing device 250 may flag the transaction as compromised and may further parse the SP database to lookup for the geolocation where user 122 sleeps. For example, if the geolocation where user 122 sleeps is frequently located in New York City, N.Y., which time is UTC/GMT −5 hours (Eastern Standard Time), but the last entry of the geolocation for the user is UTC/GMT +2, SPA computing device 250 may identify that the user is in Cape Town and approve a transaction if the time in Cape Town does not fall within the sleep time of user 122. In the example embodiment, SPA computing device 250 is configured to notify user 122, merchant 124 and/or issuer bank 130 when SPA computing device 250 detects a fraudulent transaction. In one example, SPA computing device 250 may transmit to user computing device 214 one or more notifications indicating that a transaction may be fraudulent while the user 122 is asleep. User computing device 214, which is synced with an electronic application, such as a digital wallet, uses the electronic application to receive the notification. When user 122 wakes up, user 122 may see the transaction attempt and denial. In another example, SPA computing device 250 may transmit to merchant computing device 224 and/or issuer computing device 230 one or more notifications indicating that a transaction may be fraudulent.

AB database 206 enables other parties (e.g., other merchants and banks) to access the breach data to prevent or otherwise limit fraudulent activity as a result of the data breach. In the example embodiment, AB database 206 receives the breach data from SPA computing device 250 after SPA computing device 250 has determined that a fraudulent transaction has occurred, as explained above. In one embodiment, the breached or compromised party transmits the breach data to AB database 206 directly. In other embodiments, the breach data is sent indirectly to AB database 206. For example, the breach data may be transmitted to AB database 206 via payment processor 216.

The breach data may include, but is not limited to, an account identifier, a reason code, and a timestamp for each potentially compromised payment account. The reasons code may indicate a potential origin of the data breach and/or how the potential breach was detected. The timestamp may indicate an estimated time the breach occurred, when the payment account data breach was detected, and/or when the breach was reported to AB database 206. In other embodiments, the breach data includes additional, fewer, or alternative data elements, including those described elsewhere herein. The breach data may be stored by AB database 206 for a predetermined time period to facilitate storage capacity management.

In some embodiments, SPA computing device is also in communication with HA database 208. HA database 208 is configured to store historical transaction data of historical transactions. The transaction data may be received from payment processor 216 and/or other computing devices within interchange network 128. The transaction data includes data elements retrieved and/or generated for one or more transactions processed by interchange network 128. The transaction data may include, but is not limited to, an account identifier, a timestamp (e.g., date and time), a merchant identifier, a payment amount, a payment method (e.g., card-not-present, account-on-file, etc.), a location identifier, product(s) purchased, and/or other transaction-related data elements for each transaction associated with the transaction data.

The transaction data is stored in HA database 208 as a plurality of historical authorization messages. The historical authorization messages are messages formatted based on protocols of the payment network and are used to confirm authorization of a transaction. That is, the transactions associated with the historical authorization messages are transactions that have been previously authorized. In one example, the authorization messages include ISO® 8583 compliant messages and ISO® 20022 compliant messages. As used herein, "ISO®" refers to a series of standards approved by the International Organization for Standardization (ISO is a registered trademark of the International Organization for Standardization of Geneva, Switzerland). ISO® 8583 compliant messages are defined by the ISO® 8583 standard which governs financial transaction card originated messages and further defines acceptable message types, data elements, and code values associated with such financial transaction card originated messages. ISO® 8583 compliant messages include a plurality of specified locations for data elements. ISO® 20022 compliant messages are defined by the ISO® 20022 standard. For example, ISO® 20022 compliant messages may include acceptor to issuer card messages (ATICA).

In at least some embodiments, each historical authorization message is associated with one respective transaction. In other embodiments, the authorization message may be a batch message associated with a plurality of transactions. In the example embodiment, HA database 208 is configured to be searched, parsed, sorted, and/or otherwise organized using the data elements of the historical authorization messages. For example, the historical authorization messages may be filtered to only show transaction associated with a particular merchant or a particular merchant location. In at least some embodiments, the historical authorization messages are stored by HA database 208 for a predetermined time period.

SPA computing device 250 is configured to calculate a fraud score for each user account identifier. SPA computing device 250 may use the transaction data stored in HA database 208, breach data stored in AB database 206, and the sleep pattern data stored in SP database 204 to calculate the fraud score. SPA computing device 250 may retrieve the transaction data, the breach data, sleep data, and the sleep pattern data to calculate the fraud score. SPA computing device 250 may use predefined thresholds and algorithms to calculate the fraud score. SPA computing device may transmit the retrieved transaction data, breach data, and/or sleep pattern data to issuer computing device 230, so issuer bank 130 may calculate the fraud score.

Figure 3:
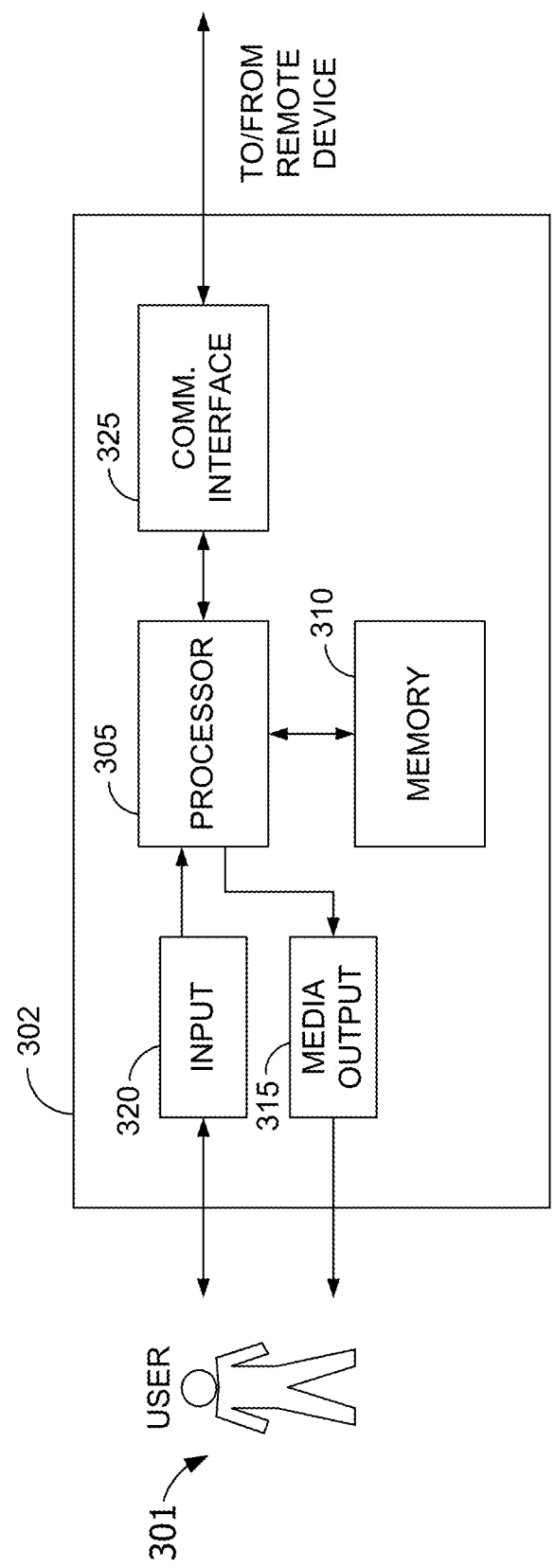

FIG. 3 illustrates an example configuration of a user system 302 operated by a user 301, such as user 122, merchant 124 (both shown in FIG. 1), or other user configured to transmit data to the SPA computing device 250 (shown in FIG. 2). User system 302 may include, but is not limited to, user computing device 214. In the example embodiment, user system 302 includes a processor 305 for executing instructions. In some embodiments, executable instructions are stored in a memory 310. Processor 305 may include one or more processing units, for example, a multi-core configuration. Memory 310 is any device allowing information such as executable instructions and/or written works to be stored and retrieved. Memory 310 may include one or more computer readable media. In some embodiment, user system 302 may be as a user computing device 214, such as a fitness wearable device (e.g., Fitbit® brand products, Jawbone® brand products, Garmin® brand products, or any other fitness wearable; Fitbit is a registered trademark of Fitbit, Inc., San Francisco, Calif.; Jawbone is a registered trademark of AliphCom, San Francisco, Calif.; Garmin is registered trademark of Garmin Ltd., Camana Bay, Cayman Islands), a web-based phone (e.g., a "smartphone"), a personal digital assistant (PDA), a "smart watch," any other wearable device, or other web-connectable device capable of monitoring the sleep pattern of user 122.

User system 302 also includes at least one media output component 315 for presenting information to user 301. User 301 may include, but is not limited to, user 122. Media output component 315 is any component capable of conveying information to user 301. For example, media output component 315 may be a display component configured to display component lifecycle data in the form of reports, dashboards, communications, or the like. In some embodiments, media output component 315 includes an output adapter, such as a video adapter and/or an audio adapter. An output adapter is operatively coupled to processor 305 and operatively connectable to an output device such as a display device, a liquid crystal display (LCD), organic light emitting diode (OLED) display, cathode ray tube (CRT), or "electronic ink" display, or an audio output device, a speaker or headphones.

In some embodiments, user system 302 includes an input device 320 for receiving input from user 301. Input device 320 may include, for example, a keyboard, a pointing device, a mouse, a stylus, a touch sensitive panel, a touch pad, a touch screen, a gyroscope, an accelerometer, a position detector, an audio input device, a fingerprint reader/scanner, a palm print reader/scanner, a iris reader/scanner, a retina reader/scanner, a profile scanner, or the like. A single component, such as a touch screen, may function as both an output device of media output component 315 and input device 320. User system 302 may also include a communication interface 325, which is communicatively connectable to a remote device, such as server system 212 (shown in FIG. 2). Communication interface 325 may include, for example, a wired or wireless network adapter or a wireless data transceiver for use with a mobile phone network, Global System for Mobile communications (GSM), 3G, 4G, Bluetooth™, or other mobile data network or Worldwide Interoperability for Microwave Access (WIMAX).

Stored in memory 310 are, for example, computer readable instructions for providing a user interface to user 301 via media output component 315 and, optionally, receiving and processing input from input device 320. A user interface may include, among other possibilities, a web browser, and client application (e.g., an electronic application). Web browsers enable users, such as user 301, to display and interact with media and other information typically embedded on a web page or a website from server system 212. A client application allows user 301 to interact with a server application from server system 212.

Figure 4:
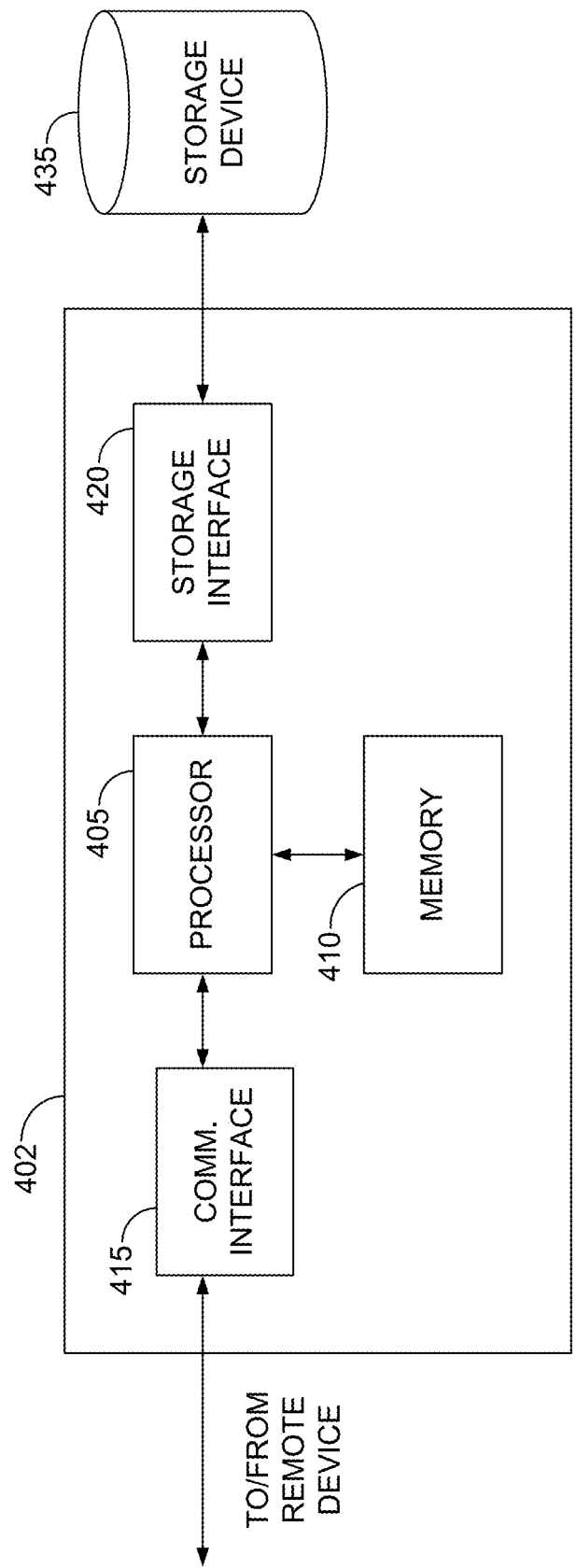

FIG. 4 illustrates an example configuration of a server system 402 such as the server system 212 (shown in FIG. 2) that includes SPA computing device 250 (shown in FIG. 2). Server system 402 may include, but is not limited to, a database server (not shown) or SPA computing device 250. In some embodiments, server system 402 is similar to server system 212.

Server system 402 includes a processor 405 for executing instructions. Instructions may be stored in a memory 410, for example. Processor 405 may include one or more processing units (e.g., in a multi-core configuration) for executing instructions. The instructions may be executed within a variety of different operating systems on the server system 402, such as UNIX, LINUX, Microsoft Windows®, etc. More specifically, the instructions may cause various data manipulations on data stored in storage device 435 (e.g., create, read, update, and delete procedures). It should also be appreciated that upon initiation of a computer-based method, various instructions may be executed during initialization. Some operations may be required in order to perform one or more processes described herein, while other operations may be more general and/or specific to a particular programming language (e.g., C, C #, C++, Java, or other suitable programming languages, etc.).

Processor 405 is operatively coupled to a communication interface 415 such that server system 402 is capable of communicating with a remote device, such as a user system or another server system 402. For example, communication interface 415 may receive communications from one or more issuer computing devices associated with issuer bank 130 via the Internet, as illustrated in FIG. 2.

Processor 405 may also be operatively coupled to a storage device 435. Storage device 435 is any computer-operated hardware suitable for storing and/or retrieving data. In some embodiments, storage device 435 is integrated in server system 402. In other embodiments, storage device 435 is external to server system 402 and is similar to, SP database 204, AB database 206, and HA database 208 (shown in FIG. 2). For example, server system 402 may include one or more hard disk drives as storage device 435. In other embodiments, storage device 435 is external to server system 402 and may be accessed by a plurality of server systems 402. For example, storage device 435 may include multiple storage units such as hard disks or solid state disks in a redundant array of inexpensive disks (RAID) configuration. Storage device 435 may include a storage area network (SAN) and/or a network attached storage (NAS) system.

In some embodiments, processor 405 is operatively coupled to storage device 434 via a storage interface 420. Storage interface 420 is any component capable of providing processor 405 with access to storage device 435. Storage interface 420 may include, for example, an Advanced Technology Attachment (ATA) adapter, a Serial ATA (SATA) adapter, a Small Computer System Interface (SCSI) adapter, a RAID controller, a SAN adapter, a network adapter, and/or any component providing processor 405 with access to storage device 435.

Memory 410 may include, but is not limited to, random access memory (RAM) such as dynamic RAM (DRAM) or static RAM (SRAM), read-only memory (ROM), erasable programmable read-only memory (EPROM), electrically erasable programmable read-only memory (EEPROM), and non-volatile RAM (NVRAM). The above memory types are exemplary only, and are thus not limiting as to the types of memory usable for storage of a computer program.

Figure 5:
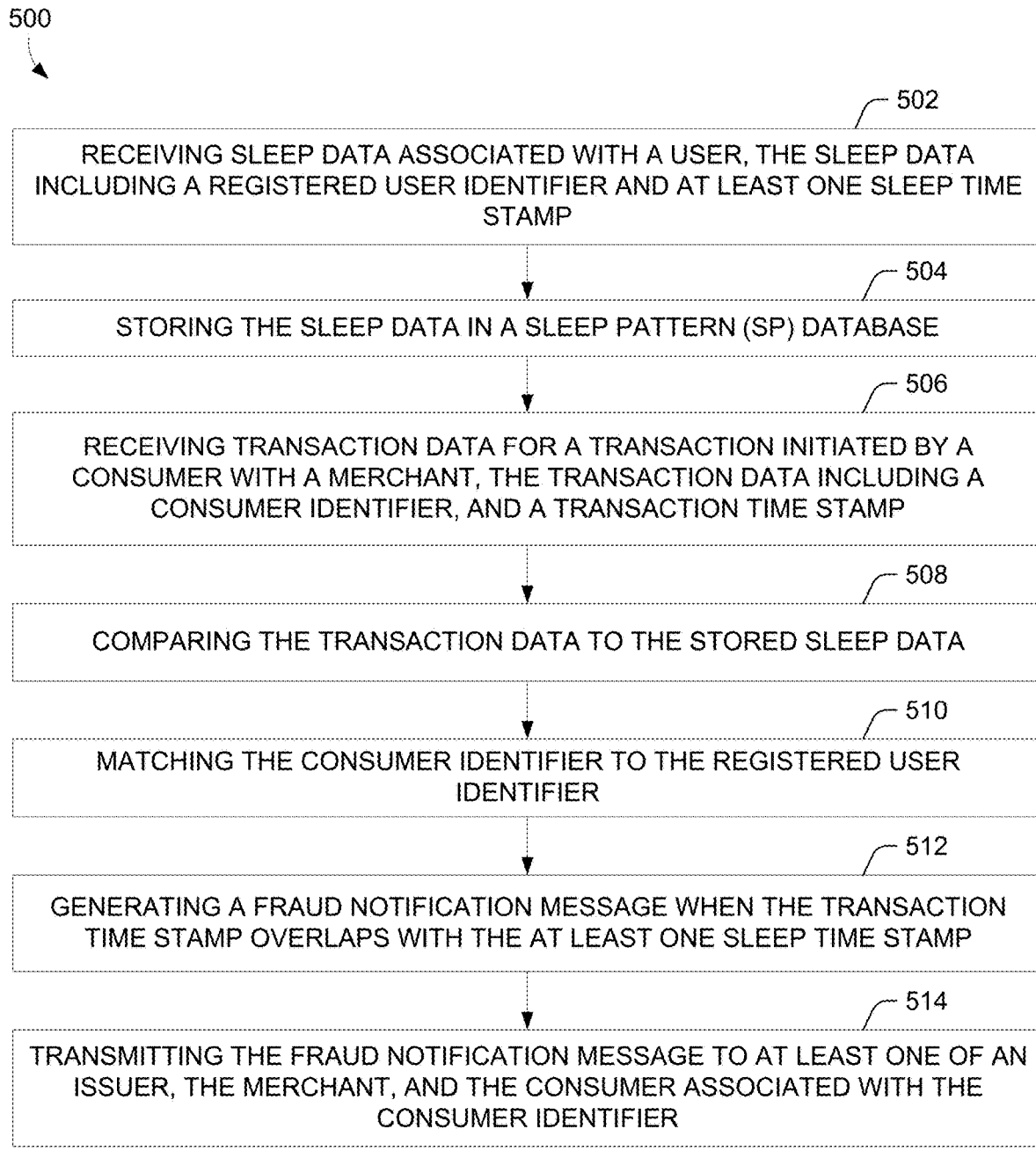

FIG. 5 is a flow diagram of an example method 500 for capturing and analyzing sleep data and sleep pattern data using a SPA system, such as SPA system 100 (shown in FIGS. 1 and 2). In the example embodiment, method 500 is performed by one or more SPA computing devices 250 (shown in FIG. 2). In certain embodiments, method 500 may be at least partially performed by a different computing device. In other embodiments, method 500 may include additional, fewer, or alternative actions, including those described elsewhere herein.

Method 500 includes receiving 502 sleep data associated with a user, the sleep data including a registered user identifier and at least one sleep time stamp, and storing 504 the sleep data in a sleep pattern (SP) database. Method 500 also includes receiving 506 transaction data for a transaction initiated by a consumer with a merchant, the transaction data including a consumer identifier, and a transaction time stamp, and comparing 508 the transaction data to the stored sleep data. Method 500 further includes matching 510 the consumer identifier to the registered user identifier, generating 512 a fraud notification message when the transaction time stamp overlaps with the at least one sleep time stamp, and transmitting 514 the fraud notification message to at least one of an issuer, the merchant, and the consumer associated with the consumer identifier.

Figure 6:
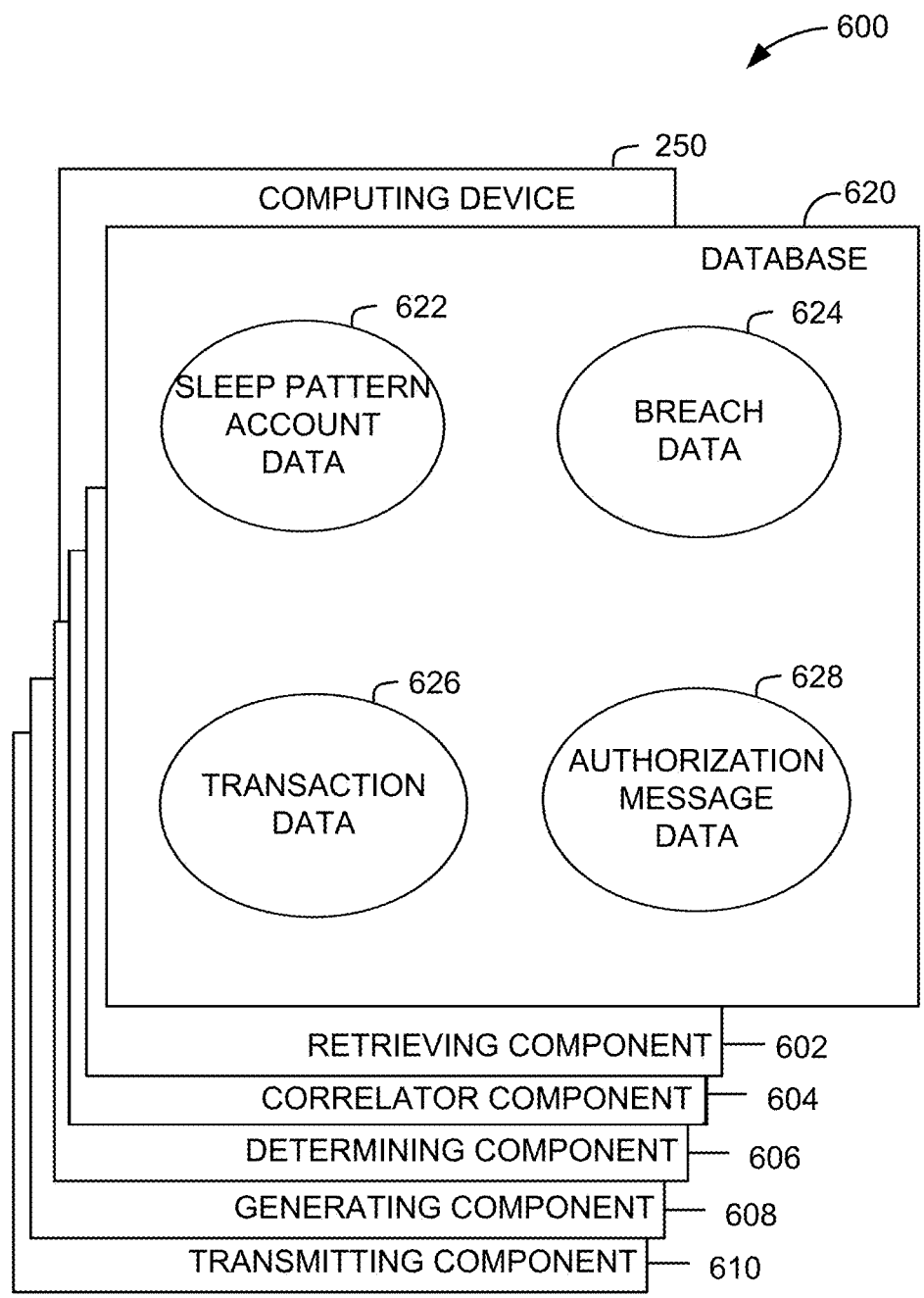

FIG. 6 is a diagram 600 of components of one or more example computing devices that may be used in the method shown in FIG. 5. FIG. 6 further shows a configuration of a distributed database system 620 including at least one SP database 204, one AB database 206, and one HA database 208, as illustrated in FIG. 2. Database system 620 is coupled to several separate components within SPA computing device 250 (shown in FIG. 2), which perform specific tasks.

SPA computing device 250 includes a retrieving component 602 configured to retrieve a set of historical account identifiers from HA database 208. SPA computing device 250 further includes a correlator component 604 configured to compare data stored in databases 204, 206, and 208. SPA computing device 250 also includes a determining component 606 configured to determine a transaction may be fraudulent. SPA computing device 250 further includes a generating component 608 configured to generate one or more fraudulent notifications when a transaction may be determined to be fraudulent. SPA computing device 250 also includes a transmitting component 610 configured to transmit the fraudulent notification to a party registered with the SP service, such as issuer bank 130, merchant, 124, and/or user 122, as illustrated in FIG. 1.

In an exemplary embodiment database system 620 is divided into a plurality of sections, including but not limited to, a sleep pattern data section 622, a breach data section 624, a transaction data section 626, and an authorization message data section 628. These sections may be separated between databases 204, 206, and 208. Databases 204, 206, and 208 are interconnected through SPA computing device 250 to update and retrieve the information as required.

As will be appreciated based on the foregoing specification, the above-discussed embodiments of the disclosure may be implemented using computer programming or engineering techniques including computer software, firmware, hardware or any combination or subset thereof. Any such resulting computer program, having computer-readable and/or computer-executable instructions, may be embodied or provided within one or more computer-readable media, thereby making a computer program product, i.e., an article of manufacture, according to the discussed embodiments of the disclosure. These computer programs (also known as programs, software, software applications, or code) include machine instructions for a programmable processor, and can be implemented in a high-level procedural and/or object-oriented programming language, and/or in assembly/machine language. As used herein, the terms "machine-readable medium," "computer-readable medium," and "computer-readable media" refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The "machine-readable medium," "computer-readable medium," and "computer-readable media," however, do not include transitory signals (i.e., they are "non-transitory"). The term "machine-readable signal" refers to any signal used to provide machine instructions and/or data to a programmable processor.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A sleep pattern analyzer (SPA) system comprising one or more sleep pattern analyzer (SPA) computing devices for capturing and analyzing sleep data and sleep pattern data, the one or more SPA computing devices comprising at least one processor and a memory, the SPA system configured to:
   in response to an enrollment of a user computing device into a sleep pattern (SP) service executable by an electronic application installed in the user computing device, enable secure electronic communications with the user computing device via the electronic application, wherein the electronic application is configured to,
   in response to detecting that a user of the user computing device is asleep, continuously collect a plurality of the sleep data in real-time while the user is asleep, the plurality of the sleep data including a plurality of sleep time stamps corresponding to times when the user is determined to be asleep;
   receive, in real-time from the user computing device via the electronic application, a first set of the plurality of the sleep data associated with the user, the first set of the plurality of the sleep data including a registered user identifier associated with the user;
   store the first set of the plurality of the sleep data in a sleep pattern (SP) database;
   calculate, based on the plurality of sleep times stamps in the first set of the plurality of the sleep data, an average time when the sleep data starts to be received;
   subsequent to calculating the average time when the sleep data starts to be received, determine that a second set of the plurality of the sleep data has not been received after a predefined tolerance time by comparing the average time when the plurality of the sleep data has been received and the predefined tolerance time;
   in response to determining that the second set of the plurality of the sleep data has not been received after the predefined tolerance time, generate a status request requesting the user computing device to transmit the second set of the plurality of the sleep data;
   receive, in response to the status request, the second set of the plurality of the sleep data;
   store the second set of the plurality of the sleep data in the SP database;
   receive in real-time transaction data for a transaction initiated by a consumer with a merchant, the transaction data including a consumer identifier, and a transaction time stamp;
   match the consumer identifier to the registered user identifier;
   compare the transaction time stamp to the plurality of sleep time stamps of the second set of the plurality of the sleep data;
   in response to the transaction time stamp overlapping at least one sleep time stamp of the plurality of sleep time stamps of the second set of the plurality of the sleep data based on the comparison, determine that the transaction is potentially fraudulent, and generate a fraud notification message; and cause the user computing device, via the electronic application, to display the fraud notification message to the user in response to the user waking up.

2. The SPA system of claim 1 further configured to correlate breach data to transaction data.

3. The SPA system of claim 1 further configured to transmit the status request to the user computing device, wherein the status request includes a request to verify that the user is asleep.

4. The SPA system of claim 1 further configured to calculate a fraud score based on historical transaction data.

5. The SPA system of claim 1 further configured to flag a payment transaction when the transaction time stamp does not fall within a predefined time period of the sleep pattern data.

6. The SPA system of claim 5 further configured to flag the payment transaction when a transaction geolocation is outside a predefined distance from a stored geolocation.

7. A computer-implemented method for a capturing and analyzing sleep data and sleep pattern data, said method implemented using one or more an sleep pattern analyzer (SPA) computing devices in communication with a memory, said method comprising:

in response to an enrollment of a user computing device into a sleep pattern (SP) service executable by an electronic application installed in the user computing device, enabling secure electronic communications with the user computing device via the electronic application, wherein the electronic application is configured to, in response to detecting that a user of the user computing device is asleep, continuously collect a plurality of the sleep data in real-time while the user is asleep, the plurality of the sleep data including a plurality of sleep time stamps corresponding to times when the user is determined to be asleep;

receiving, in real-time from the user computing device via the electronic application, a first set of the plurality of the sleep data associated with the user, the first set of the plurality of the sleep data including a registered user identifier associated with the user;

storing the first set of the plurality of the sleep data in a sleep pattern (SP) database;

calculating, based on the plurality of sleep times stamps in the first set of the plurality of the sleep data, an average time when the sleep data starts to be received;

subsequent to calculating the average time when the sleep data starts to be received, determining that a second set of the plurality of the sleep data has not been received after a predefined tolerance time by comparing the average time when the plurality of the sleep data has been received and the predefined tolerance time;

in response to determining that the second set of the plurality of the sleep data has not been received after the predefined tolerance time, generating a status request requesting the user computing device to transmit the second set of the plurality of the sleep data;

receiving, in response to the status request, the second set of the plurality of the sleep data;

storing the second set of the plurality of the sleep data in the SP database;

receiving in real-time transaction data for a transaction initiated by a consumer with a merchant, the transaction data including a consumer identifier, and a transaction time stamp;

matching the consumer identifier to the registered user identifier;

comparing the transaction time stamp to the plurality of sleep time stamps of the second set of the plurality of the sleep data;

in response to the transaction time stamp overlapping at least one sleep time stamp of the plurality of sleep time stamps of the second set of the plurality of the sleep data based on the comparison, determining that the transaction is potentially fraudulent, and generating a fraud notification message; and causing the user computing device, via the electronic application, to display the fraud notification message to the user in response to the user waking up.

8. The method of claim 7 further comprising correlating breach data to transaction data.

9. The method of claim 7 further comprising transmitting the status request to the user computing device, wherein the status request includes a request to verify that the user is asleep.

10. The method of claim 7 further comprising calculating a fraud score based on historical transaction data.

11. The method of claim 7 further configured to flag a payment transaction when the transaction time stamp does not fall within a predefined time period of the sleep pattern data.

12. The method of claim 11 further configured to flag the payment transaction when a transaction geolocation is outside a predefined distance from a stored geolocation.

13. A non-transitory computer-readable storage media having computer-executable instructions embodied thereon, wherein when executed by one or more sleep pattern analyzer (SPA) computing devices for capturing and analyzing sleep data and sleep pattern data, the one or more SPA computing devices having at least one processor coupled to at least one memory device, the computer-executable instructions cause the processor to:

in response to an enrollment of a user computing device into a sleep pattern (SP) service executable by an electronic application installed in the user computing device, enable secure electronic communications with the user computing device via the electronic application, wherein the electronic application is configured to, in response to detecting that a user of the user computing device is asleep, continuously collect a plurality of the sleep data in real-time while the user is asleep, the plurality of the sleep data including a plurality of sleep time stamps corresponding to times when the user is determined to be asleep;

receive, in real-time from the user computing device via the electronic application, a first set of the plurality of the sleep data associated with the user, the first set of the plurality of the sleep data including a registered user identifier associated with the user;

store the first set of the plurality of the sleep data in a sleep pattern (SP) database;

calculate, based on the plurality of sleep times stamps in the first set of the plurality of the sleep data, an average time when the sleep data starts to be received;

subsequent to calculating the average time when the sleep data starts to be received, determine that a second set of the plurality of the sleep data has not been received after a predefined tolerance time by comparing the average time when the plurality of the sleep data has been received and the predefined tolerance time;

in response to determining that the second set of the plurality of the sleep data has not been received after the predefined tolerance time, generate a status request requesting the user computing device to transmit the second set of the plurality of the sleep data;

receive, in response to the status request, the second set of the plurality of the sleep data;

store the second set of the plurality of the sleep data in the SP database;

receive in real-time transaction data for a transaction initiated by a consumer with a merchant, the transaction data including a consumer identifier, and a transaction time stamp;

match the consumer identifier to the registered user identifier;

compare the transaction time stamp to the plurality of sleep time stamps of the second set of the plurality of the sleep data;

in response to the transaction time stamp overlapping at least one sleep time stamp of the plurality of sleep time stamps of the second set of the plurality of the sleep data based on the comparison, determine that the transaction is potentially fraudulent, and generate a fraud notification message; and cause the user computing device, via the electronic application, to display the fraud notification message to the user in response to the user waking up.

14. The computer-executable instructions of claim 13 further cause the processor to correlate breach data to transaction data.

15. The computer-executable instructions of claim 13 further cause the processor to transmit the status request to the user computing device, wherein the status request includes a request to verify that the user is asleep.

16. The computer-executable instructions of claim 13 further cause the processor to calculate a fraud score based on historical transaction data.

17. The computer-executable instructions of claim 13 further configured to flag a payment transaction when the transaction time stamp does not fall within a predefined time period of the sleep pattern data.

18. The computer-executable instructions of claim 17 further configured to flag the payment transaction when a transaction geolocation is outside a predefined distance from a stored geolocation.

19. The SPA system of claim 1 further configured to:
automatically decline, in real time, the transaction in response to determining that transaction is potentially fraudulent.

20. The SPA system of claim 1 further configured to:
transmit, in real time, the fraud notification message to at least one of an issuer and a merchant associated with the transaction.

* * * * *